(12) United States Patent
Thomas et al.

(10) Patent No.: US 10,077,552 B2
(45) Date of Patent: Sep. 18, 2018

(54) GYPSUM PANELS, SYSTEMS, AND METHODS

(71) Applicant: Georgia-Pacific Gypsum LLC, Atlanta, GA (US)

(72) Inventors: Vincent B. Thomas, Bogart, GA (US); Rochelle Bradford, Decatur, GA (US); Christopher J. Sanders, Southaven, MS (US); Yi-Hsien Harry Teng, Westerville, OH (US)

(73) Assignee: Georgia-Pacific Gypsum LLC, Atlanta, GA (US)

( * ) Notice: Subject to any disclaimer, the term of this patent is extended or adjusted under 35 U.S.C. 154(b) by 0 days.

(21) Appl. No.: 15/668,146

(22) Filed: Aug. 3, 2017

(65) Prior Publication Data

US 2017/0328056 A1     Nov. 16, 2017

Related U.S. Application Data

(60) Division of application No. 15/180,589, filed on Jun. 13, 2016, now Pat. No. 9,739,059, which is a
(Continued)

(51) Int. Cl.
*E04C 2/24* (2006.01)
*E04C 2/06* (2006.01)
(Continued)

(52) U.S. Cl.
CPC .............. *E04C 2/246* (2013.01); *B32B 13/12* (2013.01); *B32B 13/14* (2013.01);
(Continued)

(58) Field of Classification Search
CPC .......... E04B 1/665; E04B 1/6803; E04C 2/24; E04C 2/34; E04C 2/28; E04C 2/043;
(Continued)

(56) References Cited

U.S. PATENT DOCUMENTS 2,258,574 A * 10/1941 Leary ...................... E04B 2/842
                                                52/285.3
3,162,906 A    12/1964 Dudley
(Continued)

FOREIGN PATENT DOCUMENTS

CN     202925813 U     5/2013
GB        948703 A  *  2/1964  ............... E04B 1/86
(Continued)

OTHER PUBLICATIONS

International Search Report and Written Opinion for International Application No. PCT/US2016/016375 dated May 12, 2016 (17 pages).
(Continued)

*Primary Examiner* — Jeanette E Chapman
(74) *Attorney, Agent, or Firm* — Ram W. Sabnis

(57) ABSTRACT

Gypsum panels, sheathing systems, and methods of making and using the same are provided. A gypsum panel includes a gypsum core associated with a first fiberglass mat having a continuous barrier coating, the coating penetrating a portion of the first fiberglass mat opposite the gypsum core, wherein gypsum penetrates a remaining fibrous portion of the first fiberglass mat such that voids in the first fiberglass mat are substantially eliminated. A building sheathing system includes at least two gypsum panels and a seaming component to provide a seam at an interface between the gypsum panels.

17 Claims, 9 Drawing Sheets

Related U.S. Application Data continuation of application No. 15/014,821, filed on Feb. 3, 2016.

(60) Provisional application No. 62/111,357, filed on Feb. 3, 2015.

(51) Int. Cl.

| | |
|---|---|
| *C03C 25/42* | (2006.01) |
| *C03C 25/26* | (2018.01) |
| *C03C 25/47* | (2018.01) |
| *C04B 11/00* | (2006.01) |
| *C04B 14/42* | (2006.01) |
| *E04B 1/68* | (2006.01) |
| *B32B 13/12* | (2006.01) |
| *B32B 13/14* | (2006.01) |
| *E04C 2/16* | (2006.01) |
| *E04C 2/20* | (2006.01) |
| *E04C 2/34* | (2006.01) |
| *G01N 15/08* | (2006.01) |
| *E04B 1/66* | (2006.01) |
| *E04C 2/04* | (2006.01) |
| *E04C 2/26* | (2006.01) |
| *E04C 2/28* | (2006.01) |
| *C03C 25/10* | (2018.01) |
| *C03C 25/1025* | (2018.01) |
| *C03C 25/1095* | (2018.01) |
| *C04B 28/14* | (2006.01) |
| *B28B 1/08* | (2006.01) |
| *B28B 1/30* | (2006.01) |
| *C04B 111/00* | (2006.01) |

(52) U.S. Cl.
CPC ...... *C03C 25/1025* (2013.01); *C03C 25/1095* (2013.01); *C03C 25/26* (2013.01); *C03C 25/42* (2013.01); *C03C 25/47* (2018.01); *C04B 11/00* (2013.01); *C04B 14/42* (2013.01); *C04B 28/14* (2013.01); *E04B 1/665* (2013.01); *E04B 1/6803* (2013.01); *E04C 2/04* (2013.01); *E04C 2/043* (2013.01); *E04C 2/06* (2013.01); *E04C 2/16* (2013.01); *E04C 2/20* (2013.01); *E04C 2/24* (2013.01); *E04C 2/26* (2013.01); *E04C 2/28* (2013.01); *E04C 2/34* (2013.01); *G01N 15/0806* (2013.01); *B28B 1/08* (2013.01); *B28B 1/30* (2013.01); *B32B 2255/26* (2013.01); *B32B 2260/021* (2013.01); *B32B 2260/023* (2013.01); *B32B 2260/044* (2013.01); *B32B 2262/101* (2013.01); *B32B 2307/3065* (2013.01); *B32B 2307/724* (2013.01); *B32B 2307/7246* (2013.01); *B32B 2307/7265* (2013.01); *B32B 2307/73* (2013.01); *B32B 2419/00* (2013.01); *B32B 2607/00* (2013.01); *C04B 2111/00612* (2013.01); *G01N 2015/086* (2013.01)

(58) Field of Classification Search
CPC ......... E04C 2/06; C03C 25/101; C03C 25/26; B32B 2307/3065; B32B 2255/26; B32B 2307/7265; B32B 2307/7246; B32B 2607/00; B32B 2260/023; B32B 2262/101; B32B 13/12; B28B 1/08

See application file for complete search history.

(56) References Cited

U.S. PATENT DOCUMENTS

| | | | |
|---|---|---|---|
| 3,192,098 A * | 6/1965 | Phillips | E04F 13/04 |
| | | | 428/131 |
| 3,391,037 A | 7/1968 | McNulty | |
| 3,555,763 A | 1/1971 | Bloxom | |
| 3,770,468 A | 11/1973 | Knauf et al. | |
| 5,162,145 A * | 11/1992 | Schaefer | B32B 17/10036 |
| | | | 428/209 |
| 5,552,187 A | 9/1996 | Green et al. | |
| 5,718,785 A | 2/1998 | Randall | |
| 5,810,956 A * | 9/1998 | Tanis | B01F 5/0602 |
| | | | 156/244.22 |
| 6,253,530 B1 | 7/2001 | Price et al. | |
| 8,603,927 B2 | 12/2013 | Kajander | |
| 2002/0151240 A1 | 10/2002 | Smith et al. | |
| 2002/0187297 A1 | 12/2002 | Hauber et al. | |
| 2002/0187298 A1* | 12/2002 | Hauber | B28B 11/0845 |
| | | | 428/70 |
| 2003/0203191 A1 | 10/2003 | Randall et al. | |
| 2004/0209074 A1 | 10/2004 | Randall et al. | |
| 2005/0059757 A1 | 3/2005 | Bredt et al. | |
| 2005/0238863 A1 | 10/2005 | Swales et al. | |
| 2006/0065342 A1 | 3/2006 | Porter | |
| 2008/0190062 A1 | 8/2008 | Engbrecht et al. | |
| 2009/0178357 A1 | 7/2009 | Francis | |
| 2009/0223618 A1 | 9/2009 | Russell | |
| 2010/0186870 A1 | 7/2010 | Stuart et al. | |
| 2011/0257301 A1 | 8/2011 | Russell et al. | |
| 2013/0081346 A1 | 4/2013 | Kalprathipania et al. | |
| 2014/0083035 A1 | 3/2014 | Negri et al. | |
| 2014/0272404 A1 | 9/2014 | Shake et al. | |
| 2014/0311073 A1 | 10/2014 | Pool | |
| 2015/0064433 A1* | 3/2015 | Foster | B32B 9/045 |
| | | | 428/218 |
| 2015/0158999 A1* | 6/2015 | Ayambem | C08L 91/06 |
| | | | 524/42 |
| 2015/0291844 A1 | 10/2015 | Blackburn et al. | |
| 2015/0306846 A1 | 10/2015 | Xu et al. | |
| 2016/0068434 A1 | 3/2016 | Grussing et al. | |

FOREIGN PATENT DOCUMENTS

| | | | |
|---|---|---|---|
| JP | 63273792 A | * | 11/1988 |
| JP | 7238599 A | | 9/1995 |
| JP | 10205028 A | | 8/1998 |
| WO | 2004-018172 A2 | | 3/2004 |

OTHER PUBLICATIONS

International Search Report and Written Opinion for International Application No. PCT/US2016/016402 dated May 12, 2016 (20 pages).

International Search Report and Written Opinion for International Application No. PCT/US2016/016413 dated May 17, 2016 (13 pages).

Surtynol Surfactant Material Data Sheet, p. 1 (Year: 2017).

* cited by examiner

GYPSUM PANELS, SYSTEMS, AND METHODS

CROSS-REFERENCE TO RELATED APPLICATIONS

This application is a divisional of U.S. patent application Ser. No. 15/180,589, filed on Jun. 13, 2016, which is a continuation of U.S. patent application Ser. No. 15/014,821, filed on Feb. 3, 2016, which claims priority benefit of U.S. Provisional Application No. 62/111,357, filed Feb. 3, 2015, which are each incorporated by reference herein.

FIELD

The present invention relates generally to the field of panels and systems for use in building construction, and more particularly to gypsum panels and systems of gypsum panels having water-resistive and air-barrier properties.

BACKGROUND

Many modern building codes require the use of barriers in construction to protect the building from air and water penetration. For example, building codes in eastern Canada and the northeastern United States now require air barriers to be used in all construction. Moreover, the existing International Building Code/International Residential Code (IBC/IRC) requires the use of a water-resistive air barrier for all new construction. Water-resistive air barriers may be formed from a variety of materials and structures and applied to the surface of construction sheathing materials (e.g., gypsum panels, oriented strand board (OSB) panels).

Traditionally, three types of water-resistive air barriers may be used to meet building codes. First, fabric-type membranes, or "wraps," may be used to cover the surface of building sheathing panels. However, these fabric wraps are typically unable to withstand wind conditions, suffer from drooping, and are difficult to install at heights. Moreover, the standard method of attaching such fabric membranes to sheathing panels is stapling, which compromises the effectiveness of the membrane as an air or water barrier.

Second, a liquid coating water-resistive air-barrier membrane may be applied to sheathing panels. However, these liquid coatings must be applied in the field by qualified contractors, which is time intensive and costly. Moreover, although liquid coatings serve as an effective water barrier, they provide low water vapor permeance, which affects the wall's ability to dry should it get wet during service (e.g., around window penetrations, flashing).

Third, self-adhered, or "peel and stick," water-resistive air-barrier membranes may be applied to sheathing panels. However, these self-adhered membranes are generally not permeable and therefore are not an option in many projects, because the architect or engineer must account for this impermeability in designing the building, to prevent the potential for moisture being trapped inside the wall cavity. Furthermore, self-adhered membranes require the sheathing panels to be dry and often primed prior to application, which significantly slows down the construction process.

Accordingly, it would be desirable to provide improved external sheathing panels and building sheathing systems having water-resistive and air-barrier properties, as well as methods of making such panels.

SUMMARY

In one aspect, a gypsum panel is provided, including a gypsum core associated with a first fiberglass mat having a continuous barrier coating, the coating penetrating a portion of the first fiberglass mat opposite the gypsum core, wherein gypsum crystals of the gypsum core penetrate a remaining fibrous portion of the first fiberglass mat such that voids in the first fiberglass mat are substantially eliminated.

In another aspect, a building sheathing system is provided, including at least two gypsum panels and a seaming component configured to provide a seam at an interface between at least two of the gypsum panels. Each gypsum panel includes a gypsum core associated with a first fiberglass mat having a continuous barrier coating, the coating penetrating a portion of the first fiberglass mat opposite the gypsum core, wherein gypsum crystals of the gypsum core penetrate a remaining fibrous portion of the first fiberglass mat such that voids in the first fiberglass mat are substantially eliminated.

In yet another aspect, a method of making a gypsum panel is provided, including depositing a gypsum slurry onto a surface of a first fiberglass mat opposite a continuous barrier coating, the coating penetrating a portion of the first fiberglass mat, and allowing the gypsum slurry to set to form a gypsum core. The gypsum slurry penetrates a remaining fibrous portion of the first fiberglass mat such that voids in the first fiberglass mat are substantially eliminated.

In still another aspect, a method of constructing a building sheathing system is provided, including installing at least two gypsum panels having an interface therebetween, wherein gypsum crystals of the gypsum core of each panel penetrate a remaining fibrous portion of the first fiberglass mat such that voids in the first fiberglass mat are substantially eliminated and applying a seaming component at the interface between the at least two of the gypsum panels.

BRIEF DESCRIPTION OF THE DRAWINGS

Referring now to the drawings, which are meant to be exemplary and not limiting, and wherein like elements are numbered alike.

DETAILED DESCRIPTION

Figure 1:
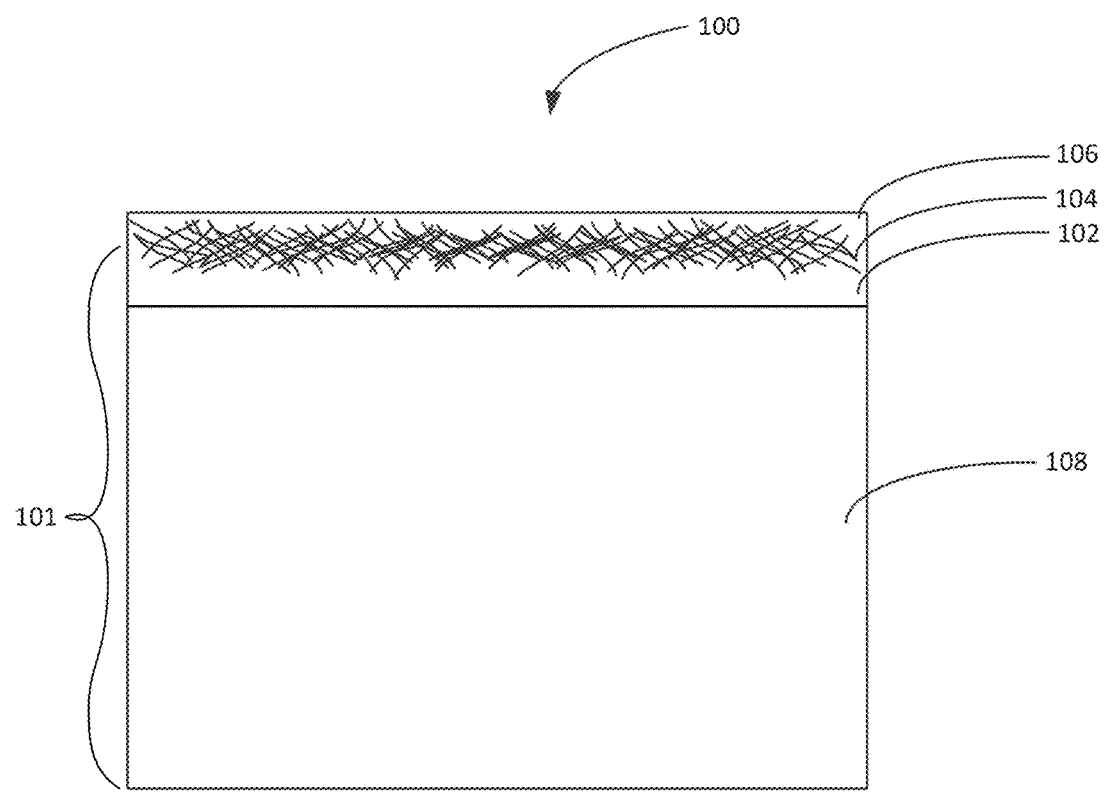
FIG. 1 is a cross-sectional view of a fiberglass faced gypsum panel having water-resistive and air-barrier properties.

Disclosed herein are gypsum panels and building sheathing systems having water-resistive and air barrier properties, as well as methods of making and using such panels and systems. These panels and systems provide advantages over commercially available water-resistive air barriers that are attached to traditional gypsum sheathing (e.g., mechanically attached flexible sheet, self-adhered sheets, fluid-applied membranes, spray foams), as well as over wood-based (e.g., oriented strand board) panels, which do not display the fire-resistance properties of gypsum panels.

As used herein, the term "water-resistive barrier" refers to the ability of a panel or system to resist liquid bulk water from penetrating, leaking, or seeping past the sheathing and into the surrounding wall components while also providing a water vapor transmission rate, or permeance, that is high enough to allow any moisture that does develop in the wall to dry. Combined with flashing around openings, such water-resistive barriers may create a shingled effect to direct water away from the sheathing and surrounding wall components. As used herein, the term "air barrier" refers to the ability of a panel or system to resist the movement of air into (infiltration) and out of (exfiltration) conditioned spaces, to create a more energy efficient structure. As used herein, the term "water-resistive air barrier" refers to the ability of a panel or system to display both water-resistive barrier and air-barrier properties.

Gypsum sheathing panels or boards may contain a set gypsum core sandwiched between two fibrous glass mats, one or both of which may be coated. The coating may be a continuous barrier coating. As used herein, the term "continuous barrier coating" refers to a coating material that is substantially uninterrupted over the surface of the fibrous mat. The continuous barrier coating may be any suitable coating material known to those of ordinary skill in the art. For example, the coating may include a polymer or resin based binder material along with one or more inorganic fillers. The continuous barrier coating may be applied on a surface of the fiberglass mat and penetrates some portion of the thickness thereof. For example, a coating may penetrate from about 5 percent to about 60 percent of the thickness of a typical fiberglass mat (e.g., about 0.04 mm to about 0.4 mm of a mat having a thickness of about 0.4 mm to about 1.0 mm). For example, a coating may penetrate from about 20 percent to about 50 percent of the thickness of a typical fiberglass mat (e.g., about 0.1 mm to about 0.3 mm of a mat having a thickness of about 0.5 mm to about 0.8 mm).

During manufacturing, a gypsum slurry may be deposited on the uncoated surface of the fiberglass mat and set to form a gypsum core of the panel. The gypsum slurry may penetrate some remaining fibrous portion of the thickness of the fiberglass mat (i.e., some portion of the fiberglass mat that is not already penetrated by the coating) and provide a mechanical bond for the panel. The gypsum slurry may be provided in one or more layers, having the same or different compositions, including one or more slate coat layers. As used herein, the term "slate coat" refers to a gypsum slurry having a higher wet density than the remainder of the gypsum slurry that forms the gypsum core.

Traditional gypsum sheathing panels do not consistently pass industry standard bulk water holdout tests and therefore are typically covered with commercially available water-resistive air barriers (e.g., mechanically attached flexible sheets, self-adhered sheets, fluid-applied membranes or coatings, sprayed foams). It has been determined that water leaks in these traditional sheathing panels are formed not only because the seams and openings are not treated, but also because water under pressure is able to penetrate though pin holes in the coating on the fiberglass mat surface and travel through the glass mat along small air pockets or channels underneath the coating and along the top of the set gypsum core. This phenomenon is especially noteworthy at or near the edges of the gypsum panel, where open pockets at the gypsum core-glass mat interface are more numerous and voluminous. These air pockets, if interconnected, allow water to travel under the glass mat coating, resulting in leaks under treated seams, openings, and fasteners.

Increasing the thickness of the coating material on the fiberglass mat has been found ineffective at providing the desired water-resistive air barrier, because the extra coating weight results in a greatly reduced water vapor transmission rate and less potential for drying wet walls in service. Higher coating weights also increase manufacturing costs and reduce the flexibility of the coated fiberglass mat, making it prone to cracking at the edges.

As such, the present disclosure is directed to providing gypsum panels and sheathing systems in which such air pockets or voids are substantially eliminated, so that the panels display the desired water-resistive and air-barrier properties independent of externally applied barrier products. Such improved sheathing panels may be combined with seaming components (i.e., components that treat the joints, or seams, between panels) to greatly reduce the cost, time, and complexity of installation of a water-resistive air barrier that provides the desired resistance to bulk water without affecting the water vapor transmission rate of the panel.

While this disclosure is generally directed to gypsum panels, it should be understood that other cementitious panel core materials are also intended to fall within the scope of the present disclosure. For example, cementitious panel core materials such as those including magnesium oxide or aluminosilicate may be substituted for the gypsum of the embodiments disclosed herein, to achieve similar results.

Improved gypsum panels, building sheathing systems, and methods for making and using the same are therefore described herein.

Panels and Systems

Gypsum sheathing panels and sheathing systems having water-resistive and air-barrier properties are provided. As shown in FIG. 1, in certain embodiments, a gypsum panel 100 includes a gypsum core 101 that is associated with a first fiberglass mat 104. The fiberglass mat 104 has a barrier coating 106 thereon, which penetrates a portion of the first fiberglass mat 104 opposite the gypsum core 101. Gypsum of the gypsum core 101 penetrates a remaining fibrous portion of the first fiberglass mat 104 such that voids in the first fiberglass mat 104 are substantially eliminated.

As used herein, the phrase "such that voids in the fiberglass mat are substantially eliminated" and similar phrases refer to the gypsum slurry (e.g., slate coat) filling all or nearly all of the interstitial volume of the fiberglass mat that is not filled by the coating material. In certain embodiments, the gypsum of the gypsum core fills at least 95 percent of the available interstitial volume of the coated fiberglass mat. In some embodiments, the gypsum core fills at least 98 percent of the available interstitial volume of the coated fiberglass mat. In further embodiments, the gypsum core fills at least 99 percent of the available interstitial volume of the coated fiberglass mat.

Such panels, in which the gypsum penetrates the mat such that the voids in the mat are substantially eliminated, may be manufactured via a variety of methods, as discussed in more detail herein. For example, the gypsum that contacts the non-coated surface of the fiberglass mat may be hydrophobic or otherwise chemically-modified for improved mat penetration, and/or mechanical means may be used to enhance penetration of the gypsum slurry into the mat.

In certain embodiments, as shown in FIG. 1, the gypsum core 101 includes two or more gypsum layers 102, 108. For example, the gypsum core may include various gypsum layers having different compositions. In some embodiments, the first gypsum layer 102 that is in contact with the fiberglass mat 104 (i.e., the layer that forms an interface with the coating material and at least partially penetrates the remaining fibrous portion of the first fiberglass mat) is hydrophobic. In some embodiments, the first gypsum layer has a wet density of from about 88 pcf to about 98 pcf. In some embodiments, the first gypsum layer has a wet density of from about 93 pcf to about 96 pcf. The first gypsum layer may be a slate coat layer. In some embodiments, the first gypsum layer 102 is present in an amount from about 5 percent to about 20 percent, by weight, of the gypsum core 101. The various gypsum layers are shown as separate layers in the figures for ease of illustration; however, it should be understood that overlap of these materials may occur at their interfaces.

In some embodiments, the slurry that forms the gypsum layer having an interface with the barrier coating includes a wetting agent to facilitate penetration of the slurry into the fibrous mat. As discussed in more detail below, the wetting agent may be any agent that reduces the surface tension of the slurry. In certain embodiments, the first gypsum layer includes a wetting agent in an amount effective to bring a slurry surface tension of the first gypsum layer to 65 dyne/cm or less. In certain embodiments, the first gypsum layer includes a wetting agent in an amount effective to bring a slurry surface tension of the first gypsum layer to 60 dyne/cm or less. In certain embodiments, the first gypsum layer includes a wetting agent in an amount effective to bring a slurry surface tension of the first gypsum layer to 55 dyne/cm or less. In certain embodiments, the first gypsum layer includes a wetting agent in an amount effective to bring a slurry surface tension of the first gypsum layer to from about 30 dyne/cm to about 55 dyne/cm. In certain embodiments, the first gypsum layer includes a wetting agent in an amount effective to bring a slurry surface tension of the first gypsum layer to from about 40 dyne/cm to about 55 dyne/cm.

Figure 2:
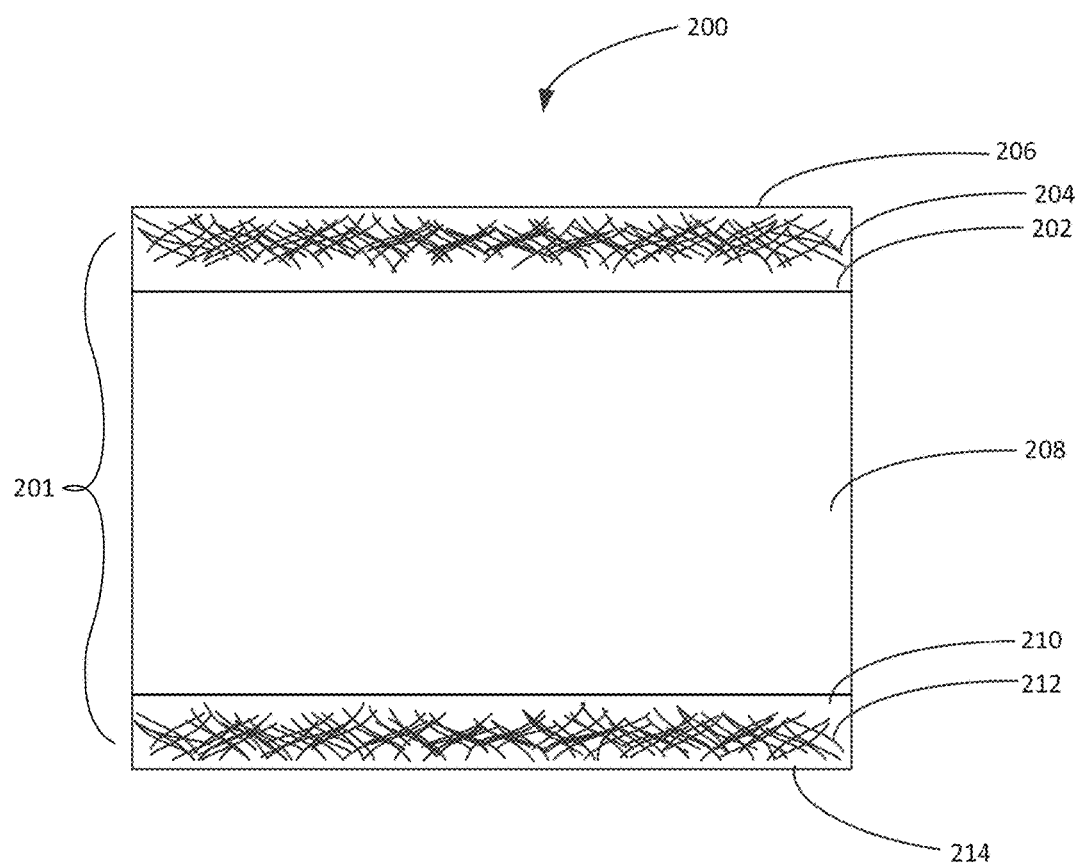
FIG. 2 is a cross-sectional view of a fiberglass faced gypsum panel having water-resistive and air-barrier properties.

In certain embodiments, as shown in FIG. 2, a gypsum panel 200 includes two fiberglass mats 204, 212 that are associated with the gypsum core 201. The second fiberglass mat 212 is present on a face of the gypsum core 201 opposite the first fiberglass mat 204. In some embodiments, only the first fiberglass mat also has a continuous barrier coating on a surface thereof. In other embodiments, both fiberglass mats 204, 212 have a coating 206, 214 on a surface thereof opposite the gypsum core 201. In some embodiments, the gypsum core 201 includes three gypsum layers 202, 208, 210. One or both of the gypsum layers 202, 210 that are in contact with the fiberglass mats 204, 212 may be a slate coat layer with hydrophobic characteristics and/or a wet density of from about 88 pcf to about 98 pcf, or of from about 93 pcf to about 96 pcf.

The layers of the gypsum core may be similar to gypsum cores used in other gypsum products, such as gypsum wallboard, dry wall, gypsum board, gypsum lath, and gypsum sheathing. For example, the gypsum core may be formed by mixing water with powdered anhydrous calcium sulfate or calcium sulfate hemihydrate, also known as calcined gypsum, to form an aqueous gypsum slurry, and thereafter allowing the slurry mixture to hydrate or set into calcium sulfate dihydrate, a relatively hard material. In certain embodiments, the gypsum core includes about 80 weight percent or above of set gypsum (i.e., fully hydrated calcium sulfate). For example, the gypsum core may include about 85 weight percent set gypsum. In some embodiments, the gypsum core includes about 95 weight percent set gypsum. The gypsum core may also include a variety of additives, such as accelerators, set retarders, foaming agents, and dispersing agents.

In certain embodiments, one or more layers of the gypsum core also include reinforcing fibers, such as chopped glass fibers. For example, the gypsum core, or any layer thereof, may include up to about 0.6 pounds of reinforcing fibers per 100 square feet of panel. For example, the gypsum core, or a layer thereof, may include about 0.3 pounds of reinforcing fibers per 100 square feet of panel. The reinforcing fibers may have a diameter between about 10 and about 17 microns and have a length between about 6.35 and about 12.7 millimeters.

The gypsum core, or one or more layers thereof, such as one or more slate coat layers, may also include an additive that improves the water-resistant properties of the core. Such additives may include, for example, poly(vinyl alcohol), optionally including a minor amount of poly(vinyl acetate); metallic resinates; wax, asphalt, or mixtures thereof, for example as an emulsion; a mixture of wax and/or asphalt and cornflower and potassium permanganate; water insoluble thermoplastic organic materials such as petroleum and natural asphalt, coal tar, and thermoplastic synthetic resins such as poly(vinyl acetate), poly(vinyl chloride), and a copolymer of vinyl acetate and vinyl chloride, and acrylic resins; a mixture of metal rosin soap, a water soluble alkaline earth metal salt, and residual fuel oil; a mixture of petroleum wax in the form of an emulsion and either residual fuel oil, pine tar, or coal tar; a mixture of residual fuel oil and rosin; aromatic isocyanates and diisocyanates; organopolysiloxanes; siliconates; wax emulsions, including paraffin, microcrystalline, polyethylene, and various co-emulsified wax emulsions; wax asphalt emulsion, each optionally with potassium sulfate, alkali, or alkaline earth aluminates, and Portland cement; a wax-asphalt emulsion prepared by adding to a blend of molten wax and asphalt, an oil-soluble, water-dispersing emulsifying agent, and admixing the aforementioned with a solution of case including, as a dispersing agent, an alkali sulfonate of a polyarylmethylene condensation product. Mixtures of these water-resistance additives may also be employed. For example, a mixture of two or more of: poly(vinyl alcohol), siliconates, wax emulsion, and wax-asphalt emulsion of the aforementioned types, may be used to improve the water resistance of the gypsum core, or gypsum slate coat layer(s) thereof.

The gypsum core, or one or more layers thereof, may also include one or more additives that enhance the inherent fire resistance of the gypsum core. Such additives may include chopped glass fibers, other inorganic fibers, vermiculite, clay, Portland cement, and other silicates, among others.

In certain embodiments, the fiberglass mat is a non-woven mat of glass fiber that is capable of forming a strong bond with the set gypsum of the gypsum core through a mechanical-like interlocking between the interstices of the fibrous mat and portions of the gypsum core. Both chopped glass strands and continuous strands may be used. For example, the glass fibers may have an average diameter of from about 10 to about 17 microns and an average length of from about ¼ inch to about 1 inch. For example, the glass fibers may have an average diameter of 13 microns (i.e., K fibers) and an average length of ¾ inch. In certain embodiments, the non-woven fiberglass mats have a basis weight of from about 1.5 pounds to about 3.5 pounds per 100 square feet of the mat. The mats may each have a thickness of from about 20 mils to about 35 mils.

The strands of the glass fibers may be bonded together to form a unitary mat structure by a suitable adhesive. For example, the adhesive may be a urea-formaldehyde resin adhesive, optionally modified with a thermoplastic extender or cross-linker, such as an acrylic cross-linker, or an acrylate adhesive resin.

As discussed above, the continuous barrier coating on the fiberglass mat may be any suitable coating known in the art. For example, the coating may include a binder material and, optionally, a filler. In certain embodiments, the coating contains filler in an amount from about 75 to about 97 weight percent. For example, the coating may contain filler in an amount from about 80 to about 95 weight percent. In one embodiment, the mat coating has a basis weight from about 3 pounds to about 9 pounds of solids per 100 square feet of the fiberglass mat. In certain embodiments, the binder is a polymer material. In certain embodiments, the coating on the first and/or second fiberglass mat is a latex acrylic polymer containing at least one inorganic filler.

In some embodiments, the binder of the mat coating is a polymer latex adhesive. For example, the binder may be styrene-butadiene-rubber (SBR), styrene-butadiene-styrene (SBS), ethylene-vinyl-chloride (EVCl), poly-vinylidene-chloride (PVdCl) and poly(vinylidene) copolymers, modified poly-vinyl-chloride (PVC), poly-vinyl-alcohol (PVOH), ethylene-vinyl-acetate (EVA), poly-vinyl-acetate (PVA) and polymers and copolymers containing units of acrylic acid, methacrylic acid, their esters and derivatives thereof (acrylic-type polymers), such as styrene-acrylate copolymers.

In one embodiment, the binder is a hydrophobic, UV resistant polymer latex adhesive. For example, the hydrophobic, UV resistant polymer latex binder adhesive may be based on a (meth)acrylate polymer latex, wherein the (meth)acrylate polymer is a lower alkyl ester, such as a methyl, ethyl or butyl ester, of acrylic and/or methacrylic acids, and copolymers of such esters with minor amounts of other ethylenically-unsaturated copolymerizable monomers (such as styrene), which are known to the art to be suitable in the preparation of UV resistant (meth)acrylic polymer latexes.

In certain embodiments, the coating also includes water and/or other optional ingredients such as colorants (e.g., dyes or pigments), transfer agents, thickeners or rheological control agents, surfactants, ammonia compositions, defoamers, dispersants, biocides, UV absorbers, and preservatives. Thickeners may include hydroxyethyl cellulose; hydrophobically-modified ethylene oxide urethane; processed attapulgite, a hydrated magnesium aluminosilicate; and other thickeners known to those of ordinary skill in the art. For example, thickeners may include CELLOSIZE QP-09-L and ACRYSOL RM-2020NPR, commercially available from Dow Chemical Company (Philadelphia, Pa.); and ATTA-GEL 50, commercially available from BASF Corporation (Florham Park, N.J.). Surfactants may include sodium polyacrylate dispersants, ethoxylated nonionic compounds, and other surfactants known to those of ordinary skill in the art. For example, surfactants may include HYDROPALAT 44, commercially available from BASF Corporation; and DYNOL 607, commercially available from Air Products (Allentown, Pa.). Defoamers may include multi-hydrophobe blend defoamers and other defoamers known to those of ordinary skill in the art. For example, defoamers may include FOAMASTER SA-3, commercially available from BASF Corporation. Ammonia compositions may include ammonium hydroxide, for example, AQUA AMMONIA 26 BE, commercially available from Tanner Industries, Inc. (Southampton, Pa.). Biocides may include broad-spectrum microbicides that prohibit bacteria and fungi growth, antimicrobials such as those based on the active diiodomethyl-ptolylsulfone, and other compounds known to those of ordinary skill in the art. For example, biocides may include KATHON LX 1.5%, commercially available from Dow Chemical Company, POLYPHASE 663, commercially available from Troy Corporation (Newark, N.J.), and AMI-CAL Flowable, commercially available from Dow Chemical Company. Biocides may also act as preservatives. UV absorbers may include encapsulated hydroxyphenyl-triazine compositions and other compounds known to those of ordinary skill in the art, for example, TINUVIN 477DW, commercially available from BASF Corporation. Transfer agents such as polyvinyl alcohol (PVA) and other compounds known to those of ordinary skill in the art may also be included in the coating composition.

In certain embodiments, a hydrophobic latex or resin material can be included in the coating to further improve the water repellence and reduce the water infiltration and enhance bonding between glass mat and gypsum.

Fillers used in the coating may include inorganic mineral fillers, such as ground limestone (calcium carbonate), clay, mica, gypsum (calcium sulfate dihydrate), aluminum trihydrate (ATH), antimony oxide, sodium-potassium alumina silicates, pyrophyllite, microcrystalline silica, talc (magnesium silicate), and other fillers known to those of ordinary skill in the art. In certain embodiments, the filler may inherently contain a naturally occurring inorganic adhesive binder. For example, the filler may be limestone containing quicklime (CaO), clay containing calcium silicate, sand containing calcium silicate, aluminum trihydrate containing aluminum hydroxide, cementitious fly ash, or magnesium oxide containing either the sulfate or chloride of magnesium, or both. In certain embodiments, the filler may include an inorganic adhesive binder as a constituent, cure by hydration, and act as a flame suppressant. For example, the filler may be aluminum trihydrate (ATH), calcium sulfate (gypsum), and the oxychloride and oxysulfate of magnesium. For example, fillers may include MINEX 7, commercially available from the Cary Company (Addison, Ill.); IMSIL A-10, commercially available from the Cary Company; and TALCRON MP 44-26, commercially available from Specialty Minerals Inc. (Dillon, Mont.). The filler may be in a particulate form. For example, the filler may have a particle size such that at least 95% of the particles pass through a 100 mesh wire screen.

In certain embodiments, the barrier coating is present on the first and/or second fiberglass mat in an amount from about 1 pound to about 9 pounds, per 100 $ft^2$. For example, the coating may be present on the first and/or second fiberglass mat in an amount from about 2 pounds to about 8 pounds, per 100 $ft^2$.

In certain embodiments, the panels have a thickness from about ¼ inch to about 1 inch. For example, the panels may have a thickness of from about ½ inch to about ⅝ inch.

By maximizing hydrophobic gypsum slurry penetration into the side of the fiberglass mat receiving gypsum, the movement of water under the mat coating within the glass mat of the finished panel when exposed to bulk water head pressures may be substantially and adequately reduced, without significantly altering the water vapor transmission rate (i.e., the ability to dry) of the finished panel. Thus, the gypsum panels disclosed herein may have one or more improved water-resistive barrier and/or air-barrier properties.

In certain embodiments, the gypsum panel passes a hydrostatic head test against water leakage, as measured by AATCC 127-2008. In addition to hydrostatic head pressure tests, other similar tests can be used to assess bulk water resistance in the range of 0.32 inches water (1.67 psf) to 44 inches of water head pressure (228 psf). This may include but is not limited to other water head tests (such as ASTM E2140), water ponding tests, cobb tests (such as ASTM C473, ASTM D 3285, ASTM D 5795, ASTM D7433, ASTM D7281), or a chambered test aided by vacuum or negative pressure differentials. Thus, the gypsum panels described herein may pass any combination of the foregoing tests.

In certain embodiments, the gypsum panel has a water vapor permeance of at least 10 (inch-pound units per ASTM E96 wet cup method), in the field of the panel (i.e., not at the edge of the panel). In some embodiments, the gypsum panel has a water vapor permeance of at least 30 (inch-pound units per ASTM E96 wet cup method), in the field of the panel. In some embodiments, the gypsum panel has a water vapor permeance of at least 32 (inch-pound units per ASTM E96 wet cup method), in the field of the panel. In certain embodiments, the gypsum panel displays water vapor transmission properties as determined by desiccant methods or by other methods including high and low relative humidity or dynamic pressure levels.

In certain embodiments, the gypsum panel displays an air penetration resistance of 0.02 L/sm$^2$ at 75 Pa, or less, when measured according to ASTM E2178. In certain embodiments, the gypsum panel displays an air penetration resistance of 0.02 L/sm$^2$ at 300 Pa, or less, when measured according to ASTM E2178.

In certain embodiments, the gypsum panel is fire-resistant. In certain embodiments, the gypsum panel is classified as noncombustible when tested in accordance with ASTM E 136 or CAN/ULC S114 and complies with ASTM C1177 requirements for glass mat gypsum substrates designed to be used as exterior sheathing for weather barriers. In particular, a ⅝-inch panel may have increased fire resistance over other sheathing substrates, such as cellulosic-based sheathing. In some embodiments, the gypsum panel has a "Type X" designation, when measured according to ASTM E119. The gypsum panels may meet "Type X" designation when tested in accordance with ASTM E119 fire tests for both generic (Generic systems in the GA-600 Fire Resistance Design Manual) and proprietary building assembly wall designs. ASTM E119 is designed to test the duration for which a building assembly can contain a fire and retain structural integrity under a controlled fire with a standard time/temperatures curve. In certain embodiments, the gypsum panel has a level 0 flame spread index and smoke develop index, when measured according to ASTM E84. For example, when exposed to surface burning characteristics, per ASTM E84 or CAN/ULC-S102, the flame spread index and smoke develop index for the gypsum panel may be 0.

Building sheathing systems are also provided herein, and include at least two of the improved water-resistive air barrier gypsum panels described herein, including any features, or combinations of features, of the panels described herein. For example, the gypsum panels may each include a gypsum core associated with a first fiberglass mat having a barrier coating, the coating penetrating a portion of the first fiberglass mat opposite the gypsum core, wherein gypsum of the gypsum core penetrates a remaining fibrous portion of the first fiberglass mat such that voids in the first fiberglass mat are substantially eliminated.

Figure 3:
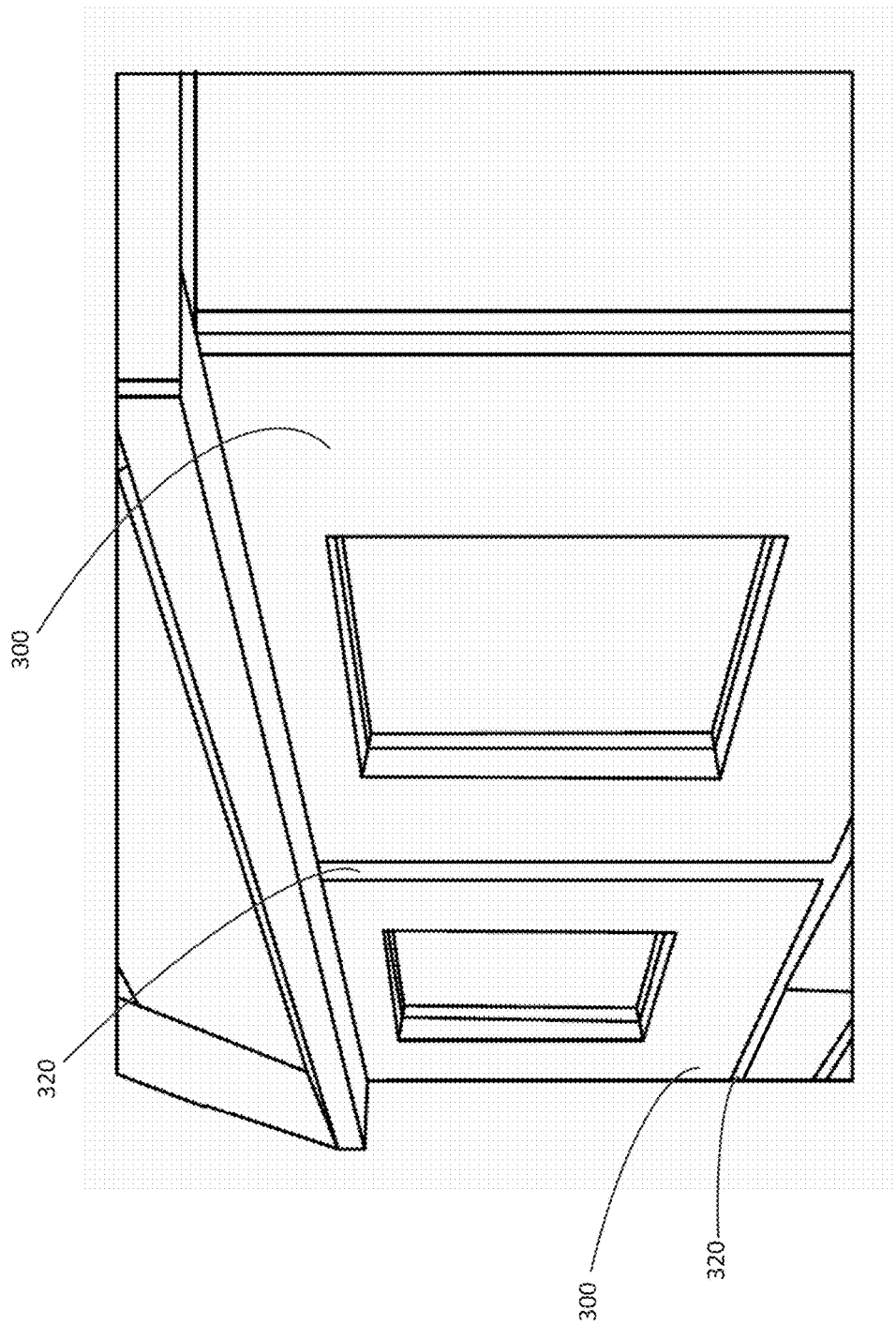
FIG. 3 is a perspective view of a building sheathing system having water-resistive and air-barrier properties.

In certain embodiments, as shown in FIG. 3, a building sheathing system includes at least two gypsum panels 300 and a seaming component 320 configured to provide a seam at an interface between at least two of the gypsum panels 300.

In certain embodiments, the seaming component comprises tape or a bonding material. For example, the seaming component may be a tape including solvent acrylic adhesives, a tape having a polyethylene top layer with butyl rubber adhesive, a tape having an aluminum foil top layer with butyl rubber adhesive, a tape having an EPDM top layer with butyl rubber adhesive, a tape having a polyethylene top layer with rubberized asphalt adhesive, or a tape having an aluminum foil top layer with rubberized asphalt adhesive. For example, the seaming component may be a bonding material such as synthetic stucco plasters, cement plasters, synthetic acrylics, sand-filled acrylics, solvent-based acrylics, solvent-based butyls, polysulfides, polyurethanes, silicones, silyl-modified polymers, water-based latexes, EVA latexes, or acrylic latexes.

Thus, the above-described enhanced panels may be installed with either a tape, liquid polymer, or other suitable material, to effectively treat areas of potential water and air intrusion, such as seams, door/window openings, penetrations, roof/wall interfaces, and wall/foundation interfaces. As such, the building sheathing panels, when used in combination with a suitable seaming component, create an effective water-resistive and/or air-barrier envelope.

Such building sheathing systems may advantageously pass any or all ICC-ES tests required for water resistant and air barrier system performance. For example, the sheathing systems may pass Sections 4.1, 4.2, 4.3, 4.4, 4.7, and/or 4.8 of the ICC-ES Acceptance Criteria for water-resistive coatings used as water-resistive barriers over exterior sheathing (ICC Evaluation Service Acceptance Criteria 212), dated February 2015. For example, the sheathing systems may pass Section 4.5 of the ICC-ES Acceptance Criteria for water-resistive membranes factory bonded to wood-based structural sheathing, used as water-resistive barriers (ICC Evaluation Service Acceptance Criteria 310), dated May 2008, revised June 2013.

In certain embodiments, the building sheathing system including at least two gypsum panels and a seaming component displays no water leaks when measured according ICC Evaluation Service Acceptance Criteria 212, Section 4. This test uses an 8' by 8' wall assembly built with multiple gypsum panels and having two vertical joint treatments and one horizontal joint treatment with seaming component(s) (as described in more detail herein) and flashing treatment with seaming component(s). The wall is subjected to 10 positive transverse load cycles of ASTM E2357 (procedure A), to racking loads of ASTM E72 to obtain a net deflection of ⅛ inch with hold-downs, and then to restrained environmental conditioning cycles as described in AC212 Section 4.7.3 for two weeks. Thus, in some embodiments, the building sheathing system displays no water leaks when measured according to ICC Evaluation Service Acceptance Criteria 212, Section 4, after being subjected to the test methods of ASTM E2357 procedure A, ASTM E72, and restrained environmental conditioning. The cycled wall is then tested under ASTM E331 water penetration with a water spray of 5 gal/ft$^2$-hr and air pressure differential of 2.86 psf maintained for 15 minutes, and resulting in no leaks within the field of the panel or cracking of sheathing or seaming components.

Thus, in some embodiments, the building sheathing system displays no water leaks when measured according to the ASTM E331 wall assembly test at an air pressure of 2.86 psf, 6.24 psf, or even 8.58 psf. The ASTM E331 test may be a water spray after a structural test and/or a test including the building transitions, openings, and penetrations. In addition to ASTM E331, other suitable tests may be substituted, such as tests using chambers that spray or flood the exposed side of the wall or are rotated to receive bulk water and create a negative air pressure differential on the inside cavity in order to expose leaks. This may include but is not limited to ASTM E547, ASTM D5957, AAMA 501, or field testing apparatus such as ASTM E1105. Thus, the building sheathing systems described herein may pass any combination of the foregoing tests.

In certain embodiments, the building sheathing system displays an air penetration resistance of 0.02 L/sm$^2$ at 75 Pa, or less, when measured according to ASTM E2178. In certain embodiments, the sheathing system displays an air penetration resistance of 0.02 L/sm$^2$ at 300 Pa, or less, when measured according to ASTM E2178.

In certain embodiments, the building sheathing system displays an exfiltration and infiltration air leakage rate of less than 0.04 cfm/ft$^2$ at 1.57 lbs/ft$^2$ (75 Pa), when measured according to the ASTM E2357 air barrier assembly test for both opaque walls and walls with penetration, when 8' by 8' walls are prepared using seaming components to seal joints, window openings, duct penetrations, pipe penetrations, external junction boxes, and masonry ties. In some embodiments, the ASTM E2357 wall assemblies, after being exposed to Q10>0.20 kPa pressure design value wind loads for sustained, cyclic, and gust loads display an air leakage infiltration and exfiltration rate of less than 0.04 cfm/ft$^2$ at 6.27 lbs/ft$^2$ (300 Pa). In certain embodiments, the building sheathing system displays an exfiltration and infiltration air leakage rate of less than 0.02 cfm/ft$^2$ at 1.57 lbs/ft$^2$ (75 Pa), when measured according to the ASTM E2357 air barrier assembly test for both opaque walls and walls with penetration. In addition to ASTM E 2357, other tests may be used to quantify air leakage in this range, including ASTM E283, ASTM E2319, ASTM E1424, ASTM E283, ASTM E1424, or similar test methods. Also, related field testing to test pressure differentials, in this range, such as ASTM E783 or related blower door apparatus testing may also be used. Thus, the building sheathing systems described herein may pass any combination of the foregoing tests.

In some embodiments, the system passes a hydrostatic head test against water leakage, as measured by AATCC 127-2008. In certain embodiments, the building sheathing system passes AATCC hydrostatic head test method 127-2008 for a 22-inch head of water (114 psf water pressure) directly over an interface of at least two gypsum panels and the seaming component, with no leaks after 5 hours. In addition to hydrostatic head pressure, other similar tests can be used to assess bulk water resistance in the range of 0.32 inches water (1.67 psf) to 44 inches of water head pressure (228 psf). This may include but is not limited to other water head tests (such as ASTM E2140), water ponding test, cobb tests (such as ASTM C473, ASTM D3285, ASTM D5795, ASTM D7433, ASTM D7281), or a chambered test aided by vacuum or negative pressure differentials. Thus, the building sheathing systems described herein may pass any combination of the foregoing tests.

In certain embodiments, the system passes AC310-2008, which tests water-resistive membranes and barriers. In some embodiments, the system passes AAMA 714 standard for liquid-applied flashing.

In certain embodiments, the sheathing system has a water vapor permeance of at least 10 (inch-pound units per ASTM E96 wet cup method). In certain embodiments, the sheathing system has a water vapor permeance of at least 20 (inch-pound units per ASTM E96 wet cup method).

Accordingly, the presently described systems are especially effective along the edges of the panel, which are traditionally more susceptible to leaks when installed in a finished system.

Thus, in certain embodiments, the sheathing system (i) passes a hydrostatic head test against water leakage, as measured by AATCC 127-2008, (ii) displays no water leaks when measured according to ICC Evaluation Service Acceptance Criteria 212, Section 4, after being subjected to the test methods of ASTM E2357 procedure A, ASTM E72, and restrained environmental conditioning, and/or (iii) displays no water leaks when measured according to ASTM E331 wall assembly test at an air pressure of 2.86 psf, 6.24 psf, or 8.58 psf. Thus, the sheathing system may display certain levels of water resistive properties. Additionally, such sheathing systems may further display desired water vapor permeance, air penetration resistance, air leakage rate, and fire resistant properties. These sheathing systems therefore provide a water resistive air barrier in the absence of any externally applied barrier product, other than the seaming component. That is, no mechanically attached flexible barrier sheet material, self-adhered barrier sheet material, fluid-applied membranes, spray foam membrane, or other barrier product need be applied to the external field of the panels to achieve the water-resistive air barrier properties.

Thus, in certain embodiments, the sheathing system includes panels having a gypsum core (one or more layers, optionally including one or more slate coat layers), a fiberglass mat facer, and a mat coating applied to the fiberglass mat facer during the panel manufacturing process, which panels display the water-resistive air barrier properties described herein, independent of any barrier product (e.g., mechanically attached flexible barrier sheet material, self-adhered barrier sheet material, fluid-applied membranes, spray foam membrane) being applied to the external surface of the panel during building construction.

Methods

Methods of making gypsum panels having water-resistive and/or air barrier properties are also provided. In certain embodiments, methods of making a gypsum panel include depositing a gypsum slurry onto a surface of a first fiberglass mat opposite a continuous barrier coating that penetrates a portion of the first fiberglass mat, and allowing the gypsum slurry to set to form a gypsum core, wherein the gypsum slurry penetrates a remaining fibrous portion of the first fiberglass mat such that voids in the first fiberglass mat are substantially eliminated. These methods may be used to produce gypsum panels having any of the features, properties, or combinations of features and/or properties, described herein.

For example, the enhanced penetration of the gypsum into the fiberglass mat may be achieved by chemical modification of the gypsum slurry, by use of a relatively high density gypsum core (or layer(s) thereof), and/or by mechanical means.

In certain embodiments, the gypsum core includes multiple layers that are sequentially applied to the fiberglass mat, and allowed to set either sequentially or simultaneously. In some embodiments, a second fiberglass mat may be deposited onto a surface of the final gypsum slurry layer (or the sole gypsum slurry layer), to form a dual mat-faced gypsum panel. For example, the second fiberglass mat may include a barrier coating on its surface that penetrates a portion of the mat.

The gypsum slurry or multiple layers thereof may be deposited on the fiberglass mat by any suitable means, such as roll coating.

In certain embodiments, depositing the gypsum slurry includes depositing a first gypsum slurry containing a wetting agent, as described in more detail below. The first gypsum slurry may contain a wetting agent in an amount effective to reduce a surface tension of the first gypsum slurry to 65 dyne/cm or less. In certain embodiments, the first gypsum slurry contains a wetting agent in an amount effective to reduce a surface tension of the first gypsum slurry to 60 dyne/cm or less. In certain embodiments, the first gypsum slurry contains a wetting agent in an amount effective to reduce a surface tension of the first gypsum slurry to 55 dyne/cm or less. In certain embodiments, the first gypsum slurry includes a wetting agent in an amount effective to reduce a surface tension of the first gypsum slurry to from about 40 dyne/cm to about 55 dyne/cm.

In certain embodiments, depositing the gypsum slurry includes depositing a first gypsum slurry having a wet density of from about 88 pcf to about 98 pcf onto the surface of a fiberglass mat, the first gypsum slurry. In certain embodiments, the first gypsum slurry has a wet density of from about 93 pcf to about 96 pcf.

In some embodiments, the gypsum core includes at least three gypsum layers, with the outermost gypsum layers of the gypsum core (i.e., the layers that form an interface with the fiberglass mats) being slate coat layers. In certain embodiments, both outermost layers have a relatively high density or are otherwise chemically altered for enhanced penetration. Thus, a third gypsum slurry may have a wet density of from about 88 pcf to about 98 pcf, or from about 93 pcf to about 96 pcf.

In certain embodiments, the first gypsum slurry (or each of the outermost gypsum slurry layers) is deposited in an amount of from about 5 percent to about 20 percent, by weight, of the gypsum core.

In certain embodiments, the gypsum slurry (or one or more layers thereof) includes a wetting agent that functions to reduce the surface tension of the gypsum slurry. In certain embodiments, the wetting agent is selected from a group consisting of surfactants, superplasticisers, dispersants, agents containing surfactants, agents containing superplasticisers, agents containing dispersants, and combinations thereof. In some embodiments, the wetting agent is present in the gypsum slurry in an amount of about 0.05 percent to about 1 percent, by weight.

Suitable surfactants and other wetting agents are selected from non-ionic, anionic, cationic, or zwitterionic compounds, such as alkyl sulfates, ammonium lauryl sulfate, sodium lauryl sulfate, alkyl-ether sulfates, sodium laureth sulfate, sodium myreth sulfate, docusates, dioctyl sodium sulfosuccinate, perfluorooctanesulfonate, perfluorobutanesulfonate, linear alkylbenzene sulfonates, alkyl-aryl ether phosphates, alkyl ether phosphate, alkyl carboxylates, sodium stearate, sodium lauroyl sarcosinate, carboxylate-based fluorosurfactants, perfluorononanoate, perfluorooctanoate, amines, octenidine dihydrochloride, alkyltrimethylammonium salts, cetyl trimethylammonium bromide, cetyl trimethylammonium chloride, cetylpyridinium chloride, benzalkonium chloride, benzethonium chloride, 5-Bromo-5-nitro-1,3-dioxane, dimethyldioctadecylammonium chloride, cetrimonium bromide, dioctadecyldimethylammonium bromide, sultaines, cocamidopropyl hydroxysultaine, betaines, cocamidopropyl betaine, phospholipids phosphatidylserine, phosphatidylethanolamine, phosphatidylcholine, sphingomyelins, fatty alcohols, cetyl alcohol, stearyl alcohol, cetostearyl alcohol, stearyl alcohols, oleyl alcohol, polyoxyethylene glycol alkyl ethers, octaethylene glycol monododecyl ether, pentaethylene glycol monododecyl ether, polyoxypropylene glycol alkyl ethers, glucoside alkyl ethers, polyoxyethylene glycol octylphenol ethers, polyoxyethylene glycol alkylphenol ethers, glycerol alkyl esters, polyoxyethylene glycol sorbitan alkyl esters, sorbitan alkyl esters, cocamide MEA, cocamide DEA, dodecyldimethylamine oxide, polyethoxylated tallow amine, and block copolymers of polyethylene glycol and polypropylene glycol. For example, suitable surfactants include Surfynol 440, Surfynol 465, Surfynol AD01, Surfynol 82, and Surfynol 61, commercially available from Air Products and Chemicals, Inc. (Allentown, Pa.).

In certain embodiments, the gypsum slurry (or one or more layers thereof) includes a hydrophobic additive. For example, the gypsum slurry or layer(s) may include wax, wax emulsions and co-emulsions, silicone, siloxane, silanes, or any combination thereof.

In certain embodiments, the gypsum slurry (or one or more layers thereof) includes a superplasticiser. For example, suitable superplasticisers include Melflux 2651 F and 4930F, commercially available from BASF Corporation.

In some embodiments, the wetting agent is present in the gypsum slurry (or layer(s) thereof) in an amount of 0.05 percent to 1.0, by weight, to reduce the slurry surface tension to about 65 dyne/cm or below, measured on the aqueous liquid after solid ingredients are filtered out. In certain embodiments, the surfactant is present in the gypsum slurry (or layer(s)) in an amount of 0.1 to 0.5 percent, by weight, with the aqueous liquid surface tension in the range between 35 dyne/cm and 55 dyne/cm. The reduced surface tension of aqueous liquid in the gypsum slurry enhances the slurry penetration into the glass mat, in reference to the pure water surface tension of 72 dyne/cm at 25° C.

In certain embodiments, there may be no residual wetting agent present in the set gypsum panel core.

In certain embodiments, the gypsum slurry (or one or more layers thereof) is substantially free of foam, honeycomb, excess water, and micelle formations. As used herein, the term "substantially free" refers to the slurry containing lower than an amount of these materials that would materially affect the performance of the panel. That is, these materials are not present in the slurry in an amount that would result in the formation of pathways for liquid water in the glass mat of a set panel, when under pressure.

In certain embodiments, the gypsum slurry (or one or more layers thereof) includes a polymer binder.

In certain embodiments, the first and/or second fiberglass mats are already coated upon contacting the gypsum slurry. In some embodiments, the methods include applying the coating to the first and/or second fiberglass mat, either before or after contacting the mats with the gypsum slurry. In certain embodiments, applying the barrier coating includes spray coating, ribbon coating, or direct roll coating. In some embodiments, the barrier coating is applied to each of the first and/or second fiberglass mats in an amount from about 1 pound to about 9 pounds, per 100 ft². For example, the barrier coating may be applied to the first and/or second fiberglass mat in an amount from about 2 pounds to about 8 pounds, per 100 ft². In other embodiments, coated fiberglass mats may be obtained in a pre-fabricated form.

In certain embodiments, the gypsum slurry (or layers thereof) may be deposited on the non-coated side of a horizontally oriented moving web of pre-coated fiberglass mat. A second coated or uncoated fiberglass mat may be deposited onto the surface of the gypsum slurry opposite the first coated fiberglass mat, e.g., a non-coated surface of the second coated fiberglass mat contacts the gypsum slurry. In some embodiments, a moving web of a pre-coated or uncoated nonwoven fibrous mat may be placed on the upper free surface of the aqueous gypsum slurry. Thus, the gypsum slurry may be sandwiched between two fiberglass mats, one or both having a barrier coating.

In some embodiments, the method also includes mechanically vibrating at least the first fiberglass mat having the first gypsum slurry deposited thereon to effect penetration of the gypsum slurry into the remaining fibrous portion of the first fiberglass mat. In certain embodiments, the method includes passing at least the first fiberglass mat having the first gypsum slurry deposited thereon over a vibration table. For example, a fiberglass mat having only one layer of gypsum slurry deposited thereon (such as the slate coat), or a fiberglass mat having multiple gypsum slurry layers, and optionally a second fiberglass mat opposite the first fiberglass mat, may be passed over a vibration table. In certain embodiments, the first fiberglass mat and gypsum slurry are passed over the vibration table prior to the panel being passed through a forming plate.

In certain embodiments, the vibration table includes at least one vibrating plate configured to display a mean vibration of from about 5 in/s to about 10 in/s. In certain embodiments, the vibration table includes at least one vibrating plate configured to vibrate at a frequency of from about 32 Hz to about 20 kHz. In some embodiments, the fiberglass mat and gypsum are passed over two sequential vibrating plates. It has been found that compared to traditional rolls having nubs thereon, the vibration tables achieve superior gypsum slurry penetration of the fiberglass mat.

In certain embodiments, allowing the gypsum slurry to set includes drying the gypsum slurry, such as in an oven or by another suitable drying mechanism.

Methods of constructing a building sheathing system, as shown in FIG. 3, are also provided herein, including installing at least two gypsum panels 300 having an interface therebetween, and applying a seaming component 320 at the interface between the at least two of the gypsum panels 300. Gypsum panels used in these methods may have any of the features, properties, or combinations of features and/or properties, described herein. Sheathing systems constructed by these methods may have any of the features, properties, or combinations or features and/or properties, described herein. The seaming component may be any suitable seaming component as described herein.

EXAMPLES

Embodiments of the water-resistive air barrier panels disclosed herein were constructed and tested, as described below.

Example 1

Fiberglass-faced gypsum panels were manufactured at two plants, in accordance with the methods disclosed herein, using the composition shown in Table 1.

TABLE 1

| Gypsum Panel Composition for Examples 1 and 2 ||
| --- | --- |
| Component (units) | Approximate Amount |
| Stucco (#/MSF) | 2200 |
| Accelerator (#/MSF) | 6 |
| Dispersant (#/MSF) | 2.0 |
| Retarder (#/MSF) | 0.3 |
| Water Repellant (#/MSF) | 11.5 |
| Water (#/MSF) | 1650 |
| Density of Slate Coat (#/ft$^3$) | Varied |
| Density of Central Slurry (#/ft$^3$) | 76 |
| Dry Weight (#/MSF) | 2630 |

Hydrostatic head tests (AATCC Test method 127-2008 and ICC Acceptance Criteria 212) were performed by testing a water column over a treated joint area. Tape or a polymer liquid was used to treat the joint between two sample sheathing panels. The seaming component spanned a ¼" gap between the two panel samples and the exterior edges were sealed with wax.

Figures 4A, 4B:
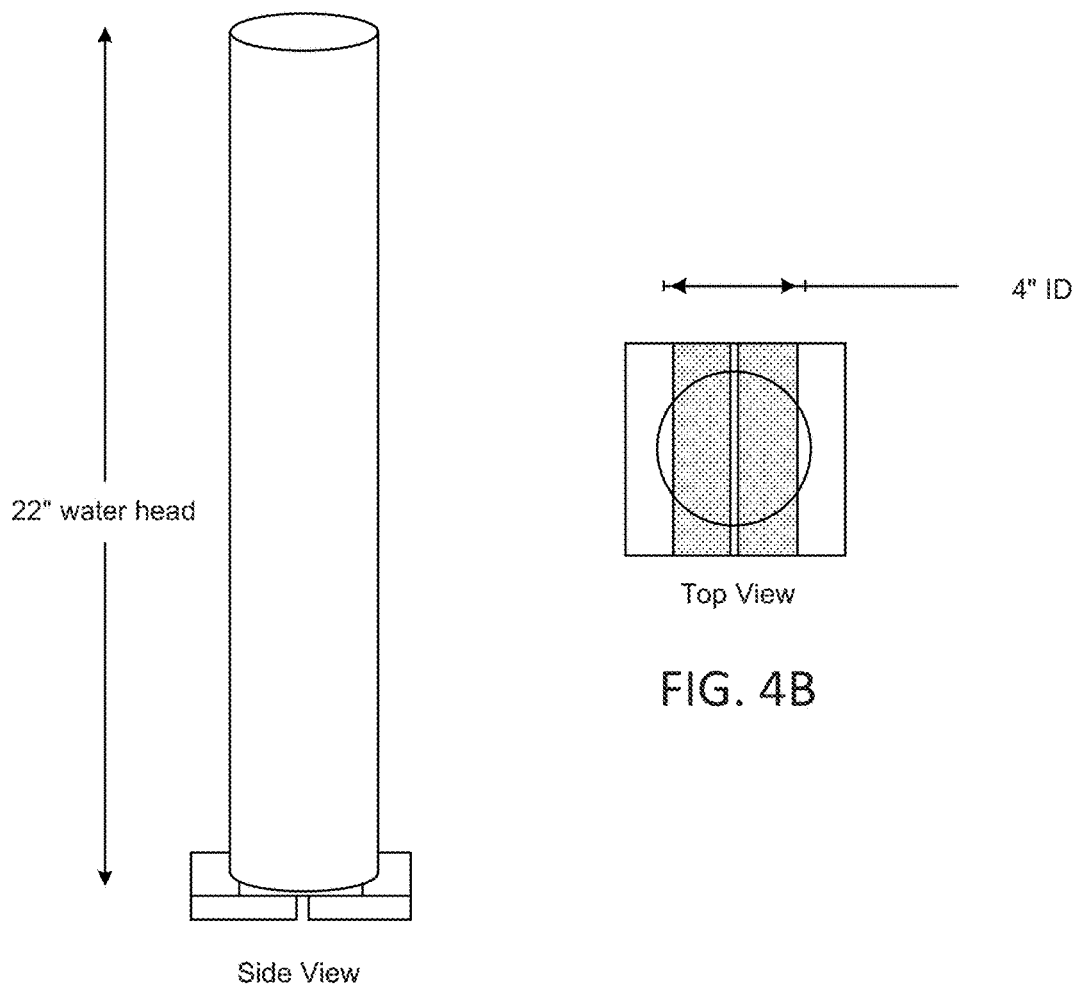
FIG. 4A is a side view of an experimental apparatus used for the hydrostatic head tests of Example 1.
FIG. 4B is a top view of an experimental apparatus used for the hydrostatic head tests of Example 1.

As shown in FIGS. 4A and 4B, a 4-inch (inner diameter) column was silicone-caulked to the surface so that it completely covered the treatment area and an untreated panel area on the edge of the tape/liquid polymer. The water column was filled with 21.6" of water and left for 5 hours. The water can be dyed and the glass mat peeled back at the end of the test to assess how much water travel occurred during the 5 hours. Water penetration on the back plane of the board or in the joint is considered a failure. With traditional gypsum panels, water tends to penetrate though the glass mat coating at the very edge of the tape/liquid polymer surface and travel along the glass mat-gypsum slurry interface to the joint.

Figure 5:
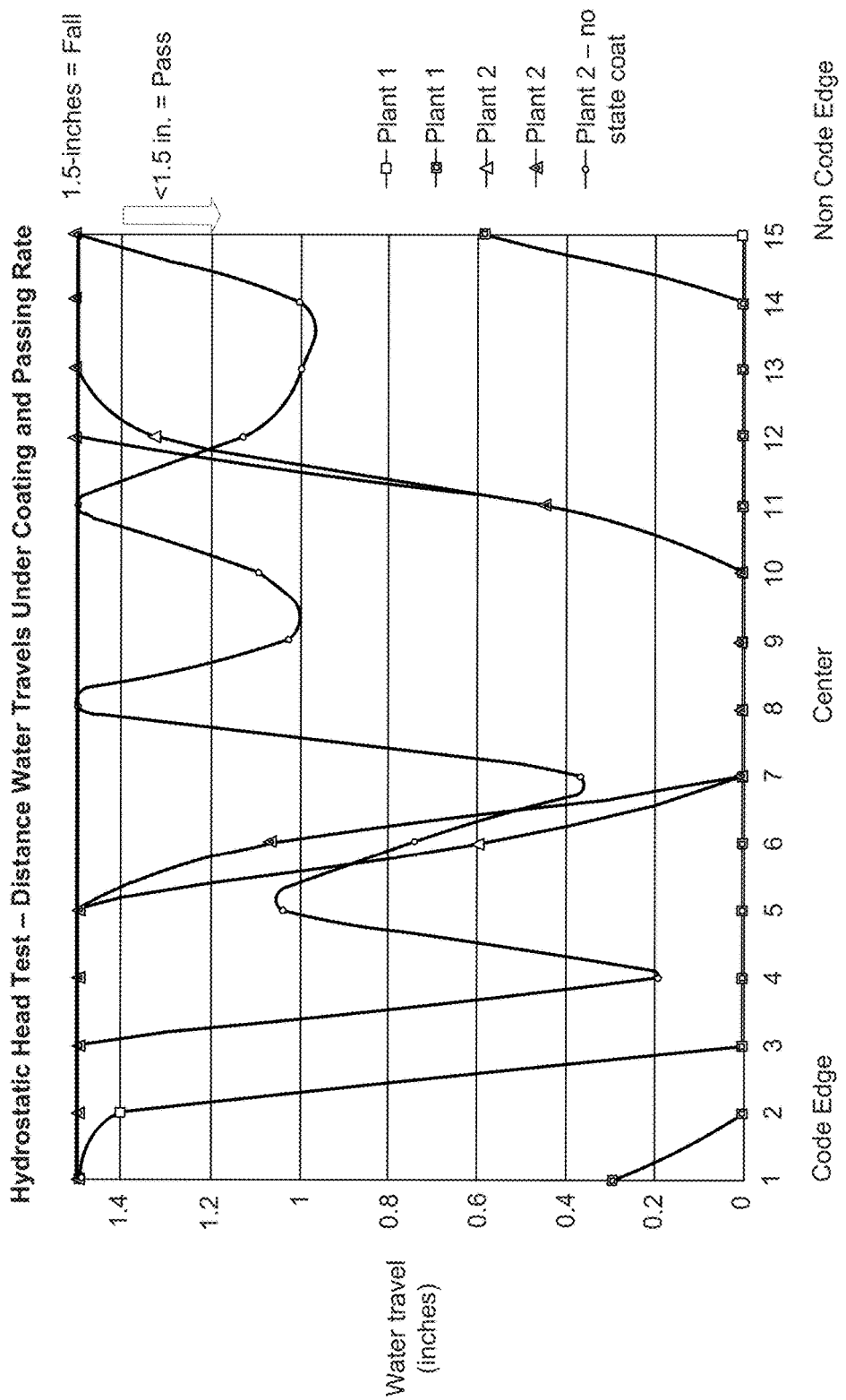
FIG. 5 is a graph showing the results of the hydrostatic head tests of Example 1.

The results of the hydrostatic head pressure testing at two different plants is shown at FIG. 5. The x-axis shows samples taken every 3" across the board width from code (timecode) edge to non-code edge. The y-axis indicates the distance of water travel at the interface area of the glass mat and slurry slate coat. A value of 1.5" indicates a leaking specimen where water has made it all the way to the joint. Plant 1 had a slate coat wet density of 95 pcf and used electric vibration tables. Plant 2 had a slate coat wet density average of 87.5 pcf and used traditional vibrator rolls. Also shown is Plant 2 with no slate coat. As is illustrated by the graph, the higher density slate coat in combination with the electric vibrator tables resulted in more consistency in passing hydrostatic head test, especially near the edge of the panel. No slate coat resulted in very inconsistent performance.

Figure 6A:
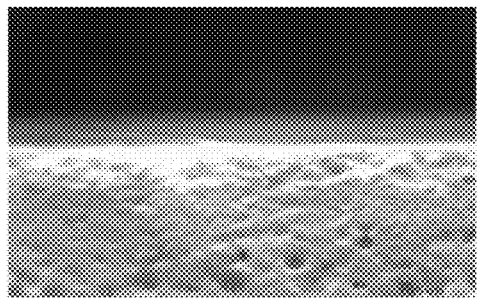
FIG. 6A is a micrograph of a cross-section of the center region of a gypsum panel of Example 1.
Figure 6B:
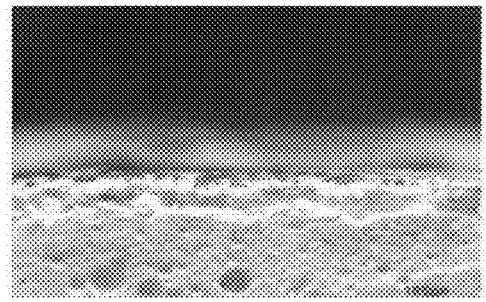
FIG. 6B is a micrograph of a cross-section of the edge region of a gypsum panel of Example 1.

FIGS. 6A and 6B are micrographs showing the cross-section of the slate coat sample made at plant 2, at the center and edges of the panel, respectively. These micrographs reveal good penetration of high density slurry near center of board.

Example 2

In another experiment, Test Sheathing A was made having the composition shown in Table 1, wherein the sheathing had a high slate coat density of 93 pcf. Two inline electric vibration tables manufactured by VIBCO (Wyoming, R.I.) mounted on isolation pads were adjusted to 33.5 Hz on the first table and 45.5 Hz on the second table, allowing for complete slate coat penetration without bleed-through. The glass mat inline mat tension was increased by increasing the brake pressure on the mat roll unwinder.

Test Sheathing B was also prepared according to the composition of Table 1 and had a slate coat density of approximately 88 pcf and used traditional vibrating rollers during panel manufacture. Both plants had the same relative amount of hydrophobic additives in the slate coat. Observations made with a 1× Nikon hand lens showed consistent slate coat penetration for Sheathing A while Sheathing B's penetration varied considerably.

Figure 7:
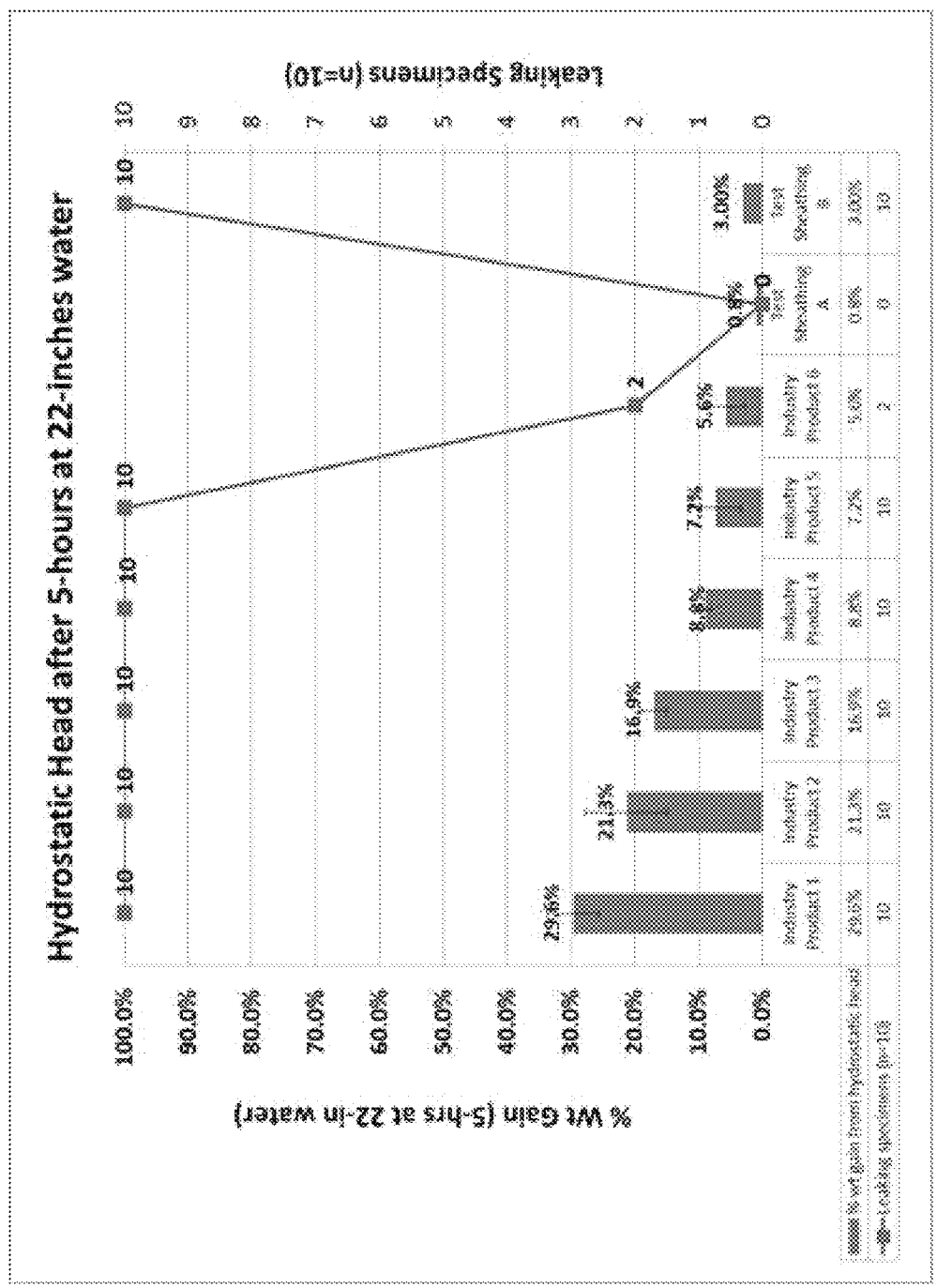
FIG. 7 is a graph showing the results of the hydrostatic head tests of Example 2.

As shown at FIG. 7, when tested in hydrostatic head pressure testing of 22" water column for 5 hours, all of the Sheathing B specimens leaked by water traveling underneath the mat surface while Sheathing B specimens showed no signs of leaks. The percentage weight gain was calculated and showed an average weight gain of 0.86% for Sheathing A and 3.0% for Sheathing B. It is believed the 5-hour percent weight gain in hydrostatic head of Sheathing A could be even further reduced by increasing the hydrophobic additive percentage in the slate coat.

Also, as shown in FIG. 7, commercially available gypsum glass mat products were purchased and tested using the same sampling procedure and test method used for Sheathings A and B. Industry Products 1-5 were commercially available gypsum glass mat sheathing products with a coated glass mat while Industry Product 6 was a gypsum glass mat sheathing product that claims >70% embedded glass mat in the gypsum face.

Results showed that Sheathing A displayed better water resistance than known coated glass mat sheathing products. Sheathing A also showed significantly better results compared to gypsum sheathing with an embedded mat (Industry Product 6) as 2 out of 10 specimens leaked compared to 0 out of 10 leaking for Sheathing A. The percent weight gain of Industry Product 6 in hydrostatic head over 5 hours was significantly higher at 5.6% compared to 0.8% for Sheathing A. It is believed that even though the mat claims 70% embedded glass mat, the unembedded portion covered with coating, density, properties of the gypsum, and/or lack of mechanical or chemical means of saturating the mat creates undesirable voids in the gypsum mat surface area, leading to leakage.

Example 3

A laboratory experiment was also conducted, in which five 12"×12" panels were manufactured, having the compositions shown in Table 2.

TABLE 2

Gypsum Panel Compositions for Example 3

| Slate Coat Condition | Slump (in) | Surfactant (Surfynol) in Slate Coat (%) | Slate Coat Wet Density (pcf) | Gypsum Core Wet Density (pcf) | Water:Stucco Ratio | Water Repellant (#/MSF) |
|---|---|---|---|---|---|---|
| 95 pcf w/o hydrophobic additive | 12.5 | 0 | 95 | 93 | 0.8 | 0 |
| 95 pcf | 12.5 | 0 | 95 | 93 | 0.8 | 11.1 |
| 95 pcf + 0.1% Surfynol | 13.5 | 0.1 | 97 | 93 | 0.8 | 11.1 |
| 83 pcf | 11.5 | 0 | 83 | 93 | 0.8 | 11.1 |
| 83 pcf + 0.1% Surfynol | 10.5 | 0.1 | 84 | 93 | 0.8 | 11.1 |

Figure 8:
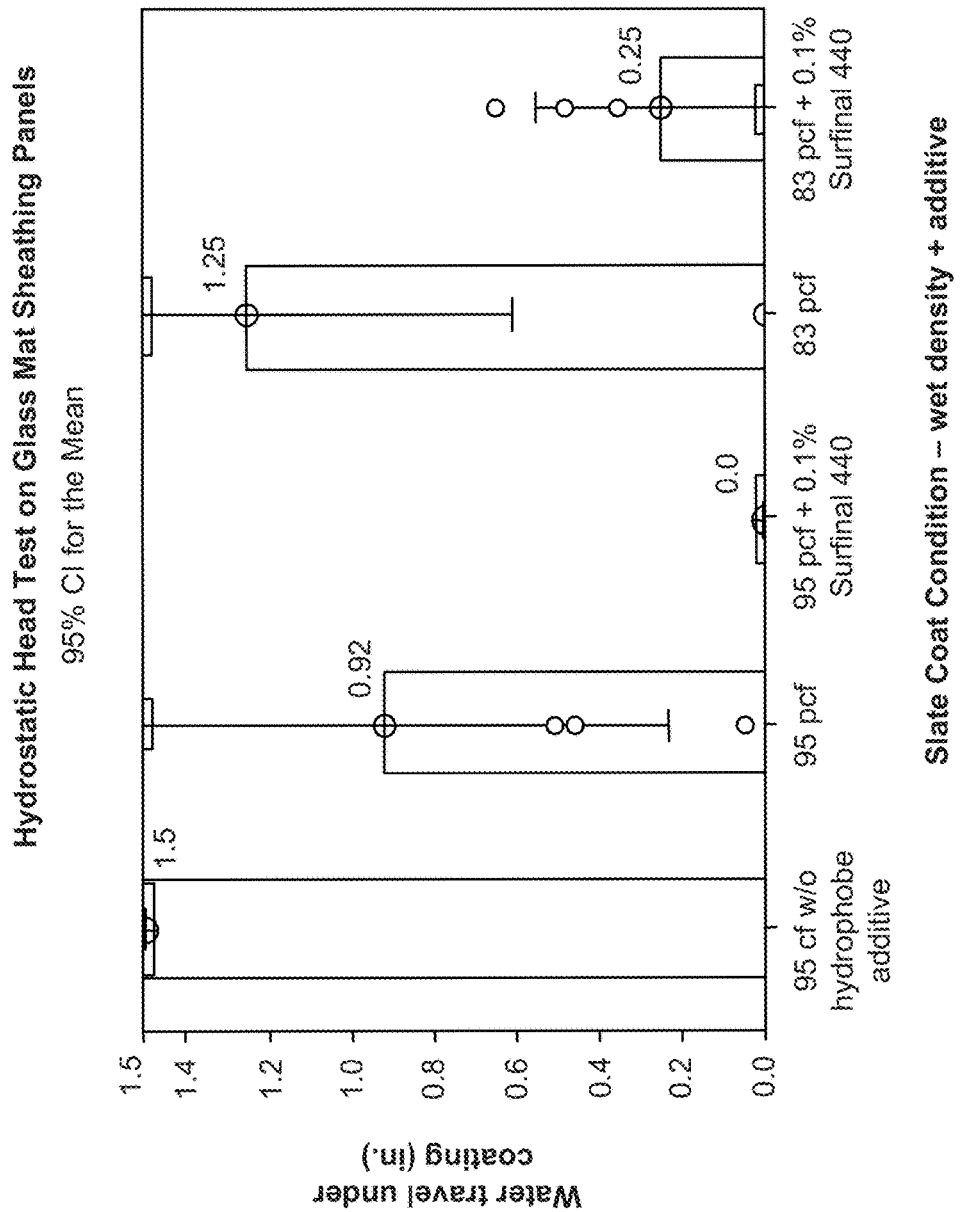
FIG. 8 is a graph showing the results of the hydrostatic head tests of Example 3.

The glass mats were slate coated before adding the core slurry, and no mechanical means (e.g., vibration) were used to increase slurry penetration. Hydrostatic head tests in accordance with those described with reference to Example 1 were performed. FIG. 8 is a graph showing the water travel under the coating in inches for five samples.

The results of this Example show that control panels without a hydrophobic additive (e.g., silicone) in the slurry failed the hydrostatic head test within the first 30 minutes, resulting in leaking at the joint. Slate coats with higher wet densities (e.g., 95 pcf) had better results than lower densities (e.g., 83 pcf). Adding a surfactant (e.g., Surfynol) to the slate coat resulted in significantly better penetration and hydrostatic head pressure test results, even at the lower densities.

Example 4

Water Vapor Transmission Testing according to ASTM E96 wet cup method was conducted for various liquid membrane products that were applied according to the manufacturer's instructions over ⅝" by 12" by 12" DENSGLASS® sheathing (manufactured by Georgia Pacific, Atlanta, Ga.). Sheathing A, per Example 2, was also tested without additional treatments. The four liquid membrane products were standard materials used in the industry and purchased from a water proofing distributer. The liquid membrane products were applied across the entire field of the DENSGLASS sheathing panels with a straight edge panel according to the manufacturers' recommended usage rates, Liquid Membrane 1=10 wet mils, Liquid Membrane 2=70 wet mils, Liquid Membrane 3=60 wet mils, and Liquid Membrane 4=10 wet mils.

Figure 9:
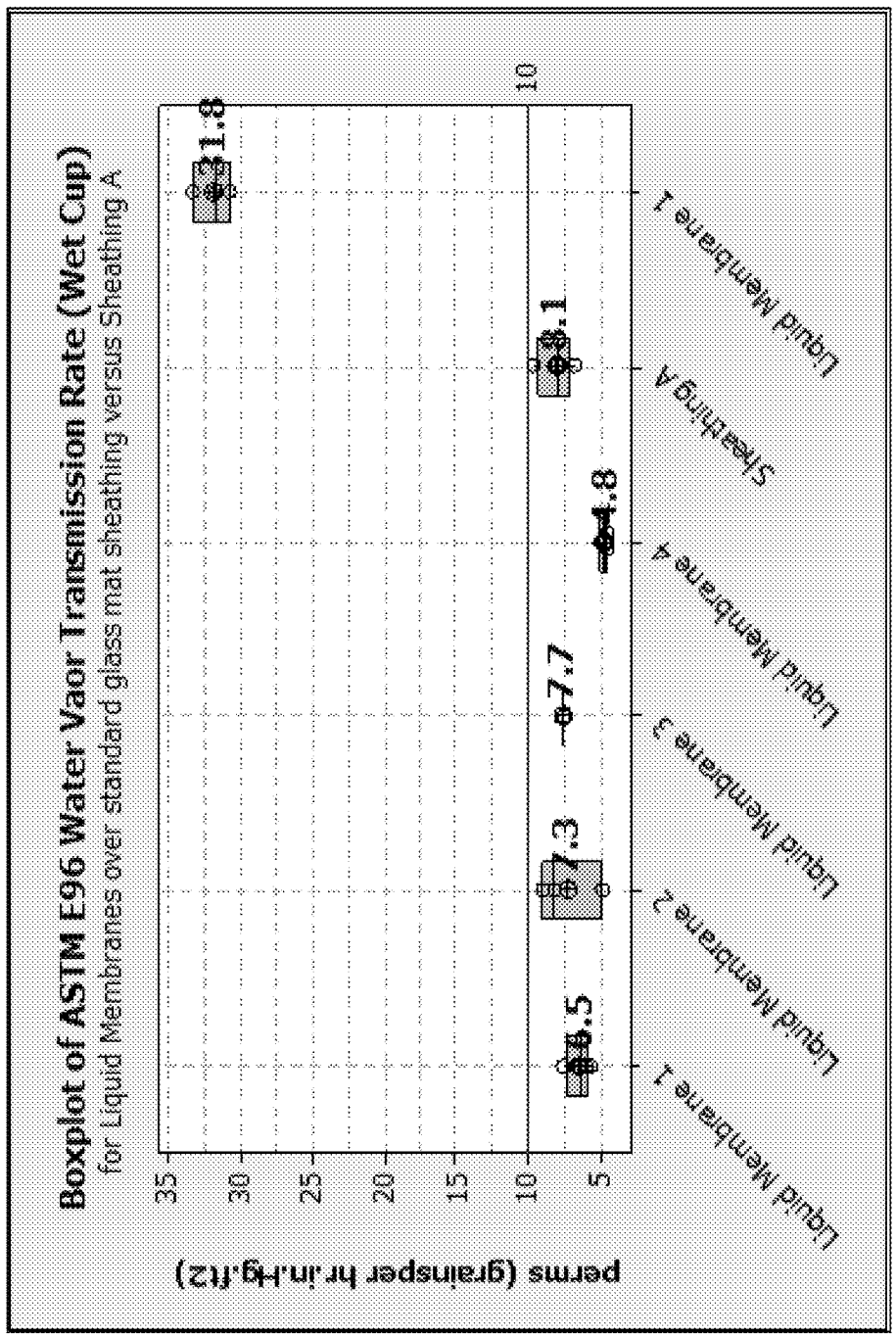
FIG. 9 is a graph showing the results of the water vapor transmission tests of Example 4.

As shown in FIG. 9, the permeance of Sheathing A was substantially higher than the permeance of the liquid membranes applied over glass mat sheathing (4.8 to 8.1 perms versus 31.6 perms), indicating the higher drying potential for such sheathing panels in-service.

Example 5

A time motion study was conducted to determine the time savings associated with the disclosed sheathing barrier system versus commercially available alternatives. Specifically, a three-story commercial building having a height of 28 feet, a total wall length of 88 feet, and a total of 2,464 gross square feet of sheathed exterior wall area was constructed. The building included 12 window openings and two door openings as well as a combination of outside and inside corners, to replicate a realistic commercial construction setting. An experienced water and air barrier installation crew installed four distinct barrier systems, including window and door flashing suitable for non-flanged commercial windows and doors, on one half of the building (i.e., approximately 1,126 net square feet of sheathed area with one door and six window openings), according to the manufacturers' installation guidelines for non-flanged windows, including coating the inside door and window openings with a fluid-applied sealant or flashing tape.

The first system included building wrap fastened with a pneumatic cap stapler to the sheathing panels. All wrap seams were overlapped and sealing with 2.5 inch tape. 6 inch self-adhesive flashing was applied to all window and door openings. The total installation time was 8 hours and 31 minutes. The second system included fluid sealant applied via a fluid gun onto fastener heads and panel seams of the sheathing system, fluid sealant applied via a fluid gun to fully flash one door and six window openings, and fluid sealant applied by roller onto the entire exterior surface of the sheathing panels. The total installation time was 10 hours and 41 minutes.

The third and fourth systems included water-resistive air barrier sheathing panels as disclosed herein. In the third system, 4-inch self-adhesive flashing was applied to the sheathing seams and corners, fluid sealant was applied to fastener heads, and 6 inch self-adhesive flashing was applied to all wind and door openings. The total installation time was 6 hours and 22 minutes. In the fourth system, fluid sealant was applied to all fastener heads, seams, and door/window openings. The total installation time was 6 hours and 26 minutes. Thus, installation of the sheathing systems including the water-resistive air barrier sheathing panels disclosed herein was accomplished in significantly less labor time as compared to known commercial building wrap and fluid sealant systems.

Thus, the gypsum sheathing panels and building sheathing systems disclosed herein display water-resistive and air-barrier properties that were previously achieved in gypsum panels only through attaching separate water-resistive air barriers (e.g., mechanically attached flexible sheet, self-adhered sheets, fluid-applied membranes, spray foams) thereto. Because gypsum panels display fire-resistance properties, these panels and systems provide advantages over wood-based (e.g., OSB) panels.

In these gypsum panels and sheathing systems, air pockets or voids are substantially eliminated, so that the panels display the desired water-resistive barrier and air-barrier properties independent of externally applied barrier products. These improved sheathing panels may be combined with seaming components (i.e., components that treat the joints, or seams, between panels) to greatly reduce the cost, time, and complexity of installation of a water-resistive air barrier that provides the desired resistance to bulk water without affecting the water vapor transmission rate of the panel. Accordingly, the disclosed system advantageously eliminates the need for applying further materials to a gypsum panel (e.g., either a membrane or liquid/foam material) to achieve water-resistive air barrier properties, when the seams are treated, and also provides fire resistance.

While the disclosure has been described with reference to a number of embodiments, it will be understood by those skilled in the art that the invention is not limited to such disclosed embodiments. Rather, the invention can be modified to incorporate any number of variations, alterations, substitutions, or equivalent arrangements not described herein, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A method of constructing a building sheathing system, comprising:
    installing at least two gypsum panels having an interface therebetween to form an external building sheathing; and
    applying a seaming component at the interface between the at least two gypsum panels,
    wherein, in the absence of any externally applied barrier product, other than the seaming component:
        the system passes a hydrostatic head test against water leakage, as measured by AATCC 127-2008,
        the system displays no water leaks when measured according to ICC Evaluation Service Acceptance Criteria 212,
        the system passes ICC Evaluation Service Acceptance Criteria 310, and/or
        the system displays no water leaks when measured according to ASTM E331 wall assembly test,
    wherein the at least two gypsum panels each comprise a gypsum core associated with a first fiberglass mat having a continuous barrier coating that comprises a plurality of pin holes that provide for water vapor transmission across the coating, the coating penetrating a portion of the first fiberglass mat opposite the gypsum core, wherein gypsum of the gypsum core penetrates a remaining fibrous portion of the first fiberglass mat such that voids in the first fiberglass mat are substantially eliminated, and
    wherein the gypsum core of each gypsum panel comprises a first gypsum layer that at least partially penetrates the remaining fibrous portion of the first fiberglass mat, the first gypsum layer being formed by a gypsum slurry that comprises a wetting agent in an amount effective to bring a slurry surface tension of the first gypsum layer from about 30 dyne/cm to about 55 dyne/cm.

2. The method of claim 1, wherein the gypsum core of each gypsum panel comprises a first gypsum layer that at least partially penetrates the remaining fibrous portion of the first fiberglass mat, the first gypsum layer having a slurry density of about 88 pcf to about 98 pcf.

3. The method of claim 1, wherein the first gypsum layer is present in an amount from about 5 percent to about 20 percent, by weight, of the gypsum core.

4. The method of claim 1, wherein the seaming component comprises tape or a bonding material.

5. The method of claim 4, wherein the seaming component comprises a bonding material selected from the group consisting of synthetic stucco plasters, cement plasters, synthetic acrylics, sand-filled acrylics, solvent-based acrylics, solvent-based butyls, polysulfides, polyurethanes, silicones, silyl-modified polymers, water-based latexes, EVA latexes, and acrylic latexes.

6. The method of claim 1, wherein the system passes AATCC hydrostatic head test method 127-2008 for a 22-inch head of water directly over the seaming component at the interface between the at least two gypsum panels, with no leaks after 5 hours.

7. The method of claim 1, wherein the system has a water vapor permeance of at least 20 inch-pound units, as measured by ASTM E96 wet cup method.

8. The method of claim 1, wherein the system displays an air leakage rate of less than 0.04 cfm/ft$^2$ at 1.57 lbs/ft$^2$, when measured according to ASTM E2357.

9. The method of claim 1, wherein the system is substantially free of any externally-applied fabric membrane, liquid coating, or self-adhered membrane.

10. A method of constructing a building sheathing system, comprising:
   installing at least two gypsum panels having an interface therebetween to form an external building sheathing, each gypsum panel comprising a gypsum core associated with a first fiberglass mat having a continuous barrier coating that comprises a plurality of pin holes that provide for water vapor transmission across the coating, the coating penetrating a portion of the first fiberglass mat opposite the gypsum core, wherein gypsum of the gypsum core penetrates a remaining fibrous portion of the first fiberglass mat such that voids in the first fiberglass mat are substantially eliminated; and
   applying a seaming component at the interface between the at least two gypsum panels,
   wherein the system is substantially free of any externally-applied fabric membrane, liquid coating, or self-adhered membrane, and
   wherein the gypsum core of each gypsum panel comprises a first gypsum layer that at least partially penetrates the remaining fibrous portion of the first fiberglass mat, the first gypsum layer being formed by a gypsum slurry that comprises a wetting agent in an amount effective to bring a slurry surface tension of the first gypsum layer from about 30 dyne/cm to about 55 dyne/cm.

11. The method of claim 10, wherein the gypsum core of each gypsum panel comprises a first gypsum layer that at least partially penetrates the remaining fibrous portion of the first fiberglass mat, the first gypsum layer having a slurry density of about 88 pcf to about 98 pcf.

12. The method of claim 10, wherein the first gypsum layer is present in an amount from about 5 percent to about 20 percent, by weight, of the gypsum core.

13. The method of claim 10, wherein the seaming component comprises tape or a bonding material.

14. The method of claim 13, wherein the seaming component comprises a bonding material selected from the group consisting of synthetic stucco plasters, cement plasters, synthetic acrylics, sand-filled acrylics, solvent-based acrylics, solvent-based butyls, polysulfides, polyurethanes, silicones, silyl-modified polymers, water-based latexes, EVA latexes, and acrylic latexes.

15. The method of claim 10, wherein the system passes AATCC hydrostatic head test method 127-2008 for a 22-inch head of water directly over the seaming component at the interface between the at least two gypsum panels, with no leaks after 5 hours.

16. The method of claim 10, wherein the system has a water vapor permeance of at least 20 inch-pound units, as measured by ASTM E96 wet cup method.

17. The method of claim 10, wherein the system displays an air leakage rate of less than 0.04 cfm/ft$^2$ at 1.57 lbs/ft$^2$, when measured according to ASTM E2357.

* * * * *